United States Patent [19]

Keller et al.

[11] Patent Number: 4,804,681

[45] Date of Patent: Feb. 14, 1989

[54] METAL COMPLEXES HAVING AN ANTINEOPLASTIC ACTION AND MEDICAMENTS CONTAINING THESE COMPLEXES

[76] Inventors: Heimo Keller, Angelweg 28, D-6900 Heidelberg; Bernhard Keppler, Wolfgangstrasse 11, D-6900 Heidelb.-Kirchh; Uwe Krüger, Neuhauser Strasse 11; Rudolf Linder, Hermann-v.-Vicaristr. 41, both of D-7750 Konstanz, all of Fed. Rep. of Germany

[21] Appl. No.: 385,653

[22] PCT Filed: Oct. 1, 1981

[86] PCT No.: PCT/EP81/00155

§ 371 Date: May 21, 1982

§ 102(e) Date: May 21, 1982

[30] Foreign Application Priority Data

Oct. 4, 1980 [DE] Fed. Rep. of Germany ....... 3037665
Dec. 19, 1980 [DE] Fed. Rep. of Germany ....... 3048109
Apr. 22, 1981 [DE] Fed. Rep. of Germany ....... 3115919
Sep. 2, 1981 [DE] Fed. Rep. of Germany ....... 3134711

[51] Int. Cl.$^4$ ..................... A61K 31/32; A61K 31/28; A61K 31/74; A61K 31/79
[52] U.S. Cl. .................... 514/493; 514/492; 424/78; 424/80; 548/402; 549/206
[58] Field of Search ............ 424/287, 78, 80; 514/492, 493; 548/402; 549/206

[56] References Cited

PUBLICATIONS

Chemical Abstracts 97:150723e (1982).
Chemical Abstracts 98:11155d (1983).
Feld et al., The Organic Chemistry of Titahiom, Washington Butterworths, 1965, p. 60.

*Primary Examiner*—Jerome D. Goldberg
*Attorney, Agent, or Firm*—Berman, Aisenberg & Platt

[57] ABSTRACT

Complexes of the general formula I

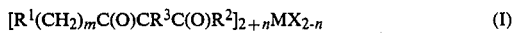

$$[R^1(CH_2)_mC(O)CR^3C(O)R^2]_{2+n}MX_{2-n} \qquad (I)$$

wherein M denotes tin, titanium, zirconium or hafnium, $R^1$ denotes hydrogen or a phenyl radical, it being possible for the phenyl radical to be monosubstituted or polysubstituted by fluorine, chlorine, bromine, nitro, $C_1$–$C_4$-alkyl, $C_1$–$C_4$-alkoxy or trifluoromethyl, $R^2$ denotes methyl or $R^1$, with the exception of hydrogen, $R^3$ denotes hydrogen or chlorine, X denotes fluorine, chlorine or bromine, but not fluorine if M denotes zirconium or hafnium, m denotes the number 1 or 0, or, if $R^1$ denotes hydrogen, the number 1 and n denotes the number 0, or, if M denotes zirconium or hafnium, the number 1 or 0, exhibit a cytostatic activity which is comparable to that of cisplatin and are less toxic than cisplatin. They are suitable for the produduction of medicaments having an anti-neoplastic action.

23 Claims, 1 Drawing Sheet

Figure 1
Median survival time
[days]

Figure 2
Median survival time
[days]

METAL COMPLEXES HAVING AN ANTINEOPLASTIC ACTION AND MEDICAMENTS CONTAINING THESE COMPLEXES

TECHNICAL FIELD

The invention relates to metal complexes having an antineoplastic action and to medicaments containing these complexes.

BACKGROUND

A medicament which contains the complex compound cis-diamminedichloroplatinum(II) has recently been marketed as a chemotherapeutic agent against cancer. This compound, known by the International Nonproprietary Name (INN) of cisplatin has proved to be an extremly potent antitumor agent, especially in the treatment of testicular tumors, and also, for example, of ovarian tumors and of oat-cell carcinomas. The disadvantage of cis-platin is its relatively high toxicity. Its nephrotoxicity and its action leading to lasting damage to hearing are particularly serious. Renal damage and damage to hearing are found with considerable frequency after administration of only a single therapeutic dose. Besides the nephrotoxic and hematotoxic action, the long-lasting severe nausea and the retching associated therewith are, above all, also extremely unpleasant for the patient. Numerous other platinum complexes (German Offenlegungsschrift No. 2,445,418, German Offenlegungsschrift No. 2,837,237, German Offenlegungsschrift No. 2,626,559 and German Offenlegungsschrift No. 2,539,179) and complex compounds of other transition metals have recently been proposed as agents having a cytostatic action. In German Offenlegungsschrift No. 2,801,355, a brown amorphous complex which is obtained by reacting ascorbic acid with a titanium(III) compound and a copper(II) compound (in a molar ratio of 36:1:6) is said to have curative and prophylactic actions against, inter alia, leukemia. It has been reported that titanocene dichloride, zirconocene dichloride and hafnocene dichloride have an inhibiting action on ascitic Ehrlich tumors in mice [P. Köpf-Maier, B. Hesse and H. Köpf, *J. Cancer Res. Clin. Onco.*, 96, 43 (1980)]. Dialkyl- tin-dihalide phenanthroline complexes and bipyridyl complexes have been said to have inhibiting actions on P388 leukemia in mice (A. J. Crowe and P. J. Smith, *Chemistry and Industry*, page 200, Mar. 1, 1980).

THE INVENTION

Surprisingly, it has now been found that complexes of formula I $$[R^1(CH_2)_mC(O)CR^3C(O)R^2]_{2+n}MX_{2-n} \quad (I)$$

wherein

M denotes tin, titanium, zirconium or hafnium;

$R^1$ denotes hydrogen, phenyl or substituted phenyl [substituted phenyl being monosubstituted or polysubstituted (independently) by fluorine, chlorine, bromine, nitro, $C_1$-$C_4$-alkyl, $C_1$-$C_4$-alkoxy or trifluoromethyl];

$R^2$ denotes methyl or one of the meanings of $R^1$ other than hydrogen;

$R^3$ denotes hydrogen (—H) or chlorine (—Cl);

X denotes fluorine (—F), chlorine (—Cl) or bromine (—Br), but not fluorine when M denotes zirconium or hafnium;

m denotes the number 1 or 0, or, when $R^1$ denotes hydrogen, only the number 1 and n denotes the number 0, or, when M denotes zirconium or hafnium, the number 1 or 0;

have a cytostatic activity which is comparable to that of cisplatin and are less toxic than cisplatin. Accordingly, compared with cisplatin, these compounds have a significantly greater therapeutic range. They are useful as chemotherapeutic agents with few side effects for the treatment of tumors, e.g. ovarian tumors, and testicular tumors. Accordingly the compounds are useful for alleviation of pain and suffering in connection with cancer therapy, remission, alleviation of symptoms and extension of life expectancy.

The complexes are alternatively represented by the following formulae:

| (A) | $[H_3C—CO—CR^3—CO—CH_3]_2SnX_2$ | (N) | $[H_3C—CO—CR^3—CO—R^4]_3ZrX°$ |
|---|---|---|---|
| (B) | $[H_3C—CO—CR^3—CO—R^4]_2SnX_2$ | (O) | $[R^4—CH_2—CO—CR^3—CO—R^2]_3ZrX°$ |
| (C) | $[R^4—CH_2—CO—CR^3—CO—R^2]_2SnX_2$ | (P) | $[R^4—CO—CR^3—CO—R^2]_3ZrX°$ |
| (D) | $[R^4—CO—CR^3—CO—R^2]_2SnX_2$ | (Q) | $[H_3C—CO—CR^3—CO—CH_3]_2HfX°_2$ |
| (E) | $[H_3C—CO—CR^3—CO—CH_3]_2TiX_2$ | (R) | $[H_3C—CO—CR^3—CO—R^4]_2HfX°_2$ |
| (F) | $[H_3C—CO—CR^3—CO—R^4]_2TiX_2$ | (S) | $[R^4—CH_2—CO—CR^3—CO—R^2]_2HfX°_2$ |
| (G) | $[R^4—CH_2—CO—CR^3—CO—R^2]_2TiX_2$ | (T) | $[R^4—CO—CR^3—CO—R^2]_2HfX°_2$ |
| (H) | $[R^4—CO—CR^3—CO—R^2]_2TiX_2$ | (U) | $[H_3C—CO—CR^3—CO—CH_3]_3HfX°$ |
| (I) | $[H_3C—CO—CR^3—CO—CH_3]_2ZrX°_2$ | (V) | $[H_3C—CO—CR^3—CO—R^4]_3HfX°$ |
| (J) | $[H_3C—CO—CR^3—CO—R^4]_2ZrX°_2$ | (W) | $[R^4—CH_2—CO—CR^3—CO—R^2]_3HfX°$ |
| (K) | $[R^4—CH_2—CO—CR^3—CO—R^2]_2ZrX°_2$ | (X) | $[R^4—CO—CR^3—CO—R^2]_3HfX°$ |
| (L) | $[R^4—CO—CR^3—CO—R^2]_2ZrX°_2$ | | |
| (M) | $[H_3C—CO—CR^3—CO—CH_3]_3ZrX°$ | | | wherein $R^2$ is methyl or one of the meanings of $R^4$;

$R^3$ is hydrogen (—H) or chloro;

$R^4$ is phenyl or substituted phenyl, any substituent of which is, independently, fluoro, chloro, bromo, nitro, alkyl having from 1 to 4 carbon atoms, alkoxy having from 1 to 4 carbon atoms or trifluoromethyl;

X is fluorine, chlorine or bromine; and

X° is chlorine or bromine.

Substituted phenyl (in the definition of $R^4$) is mono- or polysubstituted (particularly di- or tri-substituted). Polysubstitution naturally excludes combinations of substituents and positions which involve steric hindrance.

The invention thus relates to medicaments containing one or more complexes of formula I and particularly to the use of such medicaments for combating cancers.

One group of medicament compositions comprises pharmaceutically-acceptable excipient and from 0.1 to 99.5 percent by weight of metal complex of formula (I) wherein:

M is tin, titanium, zirconium or hafnium;
$R^1$ is —H or one of the meanings of $R^4$;
$R^2$ is methyl or one of the meanings of $R^4$;
$R^3$ is —H or chloro;
$R^4$ is phenyl or substituted phenyl, any substituent of which is a member selected from the group consisting of fluoro, chloro, bromo, nitro, $C_{(1-4)}$-alkyl, $C_{(1-4)}$-alkoxy and trifluoromethyl;
X is —Cl or —Br when X is zirconium of hafnium and is —Cl, —Br or —F when X is tin or titanium;
m is zero or one when $R^1$ is one of the meanings of $R^4$ and is one when $R^1$ is —H; and
n is zero when M is tin or titanium and is zero or one when M is zirconium of hafnium.

Medicaments containing one or more complexes of formula I′

(I′)

wherein
M′ denotes tin, titanium zirconium or hafnium;
$R^{1'}$ denotes a phenyl radical, which is optionally substituted by 4-chloro, 4-bromo, 3-nitro, 4-methoxy, 3,4-dimethoxy, 4-methyl or 2,4,6-trimethyl;
$R^{2'}$ denotes methyl or one of the meanings of $R^{1'}$;
$R^{3'}$ denotes hydrogen or chlorine;
X′ denotes fluorine, chlorine or bromine, but not fluorine when M′ denotes zirconium or hafnium;
m′ denotes the number 1 or 0 and
n′ denotes the number 0, or, when ′ denotes zirconium or hafnium, the number 1 or 0;
are preferred.

Medicaments containing one or more complexes of the formula I″

$$[R^{1''}C(O)CR^{3''}C(O)R^{2''}]_{2+n''}M''X''_{2-n''} \quad (I'')$$

wherein
M″ denotes tin, titanium, zirconium or hafnium;
$R^{1''}$ denotes a phenyl radical;
$R^{2''}$ denotes a methyl radical;
$R^{3''}$ denotes hydrogen or chlorine;
X″ denotes fluorine, chlorine or bromine, but not fluorine when M″ denotes zirconium or hafnium; and
n″ denotes the number 0, or, when M″ denotes zirconium or hafnium, the number 1 or 0;
are particularly preferred.

Medicaments containing compounds of the above formulae I, I′ and I″, wherein the variables M, M′ and M″, $R^1$, $R^{1'}$ and $R^{1''}$, $R^2$, $R^{2'}$ and $R^{2''}$, $R^3$, $R^{3'}$ and $R^{3''}$, n, n′ and n″ and m and m′ have the previously-noted meanings but X, X′ and X″ in each case denote only chlorine, form particular embodiments of the invention.

Medicaments containing the compounds of the above formulae I, I′ and I″, wherein the variables $R^1$, $R^{1'}$ and $R^{1''}$, $R^2$, $R^{2'}$ and $R^{2''}$, $R^3$, $R^{3'}$ and $R^{3''}$, X, X′ and X″, n, n′ and n″ and m and m′ have the previously-ascribed meanings but M, M′ and M″ in each case denote only titanium, zirconium or hafnium, and preferably titanium, form further particular embodiments of the invention.

Medicaments containing dichlorobis(benzoylacetonato)titanium(IV), dichlorobis(benzoylacetonato)zirconium(IV) and/or dichlorobis(benzoylacetonato)hafnium(IV) are particularly preferred.

The invention also relates to the use of the compounds of formula I, I′ or I″ for alleviating pain and suffering and extending life expectancy and for the production of medicaments, especially of medicaments for use against cancers.

The compounds of formula $I^a$ ($I^a$)

wherein
$M^a$ denotes tin, titanium, zirconium or hafnium;
$R^{1a}$ denotes a phenyl radical which is monosubstituted or polysubstituted by fluorine, chlorine, bromine, nitro, $C_1$-$C_4$-alkyl, $C_1$-$C_4$-alkoxy or trifluoromethyl, and, when $M^a$ represents zirconium or hafnium, $R^{1a}$ additionally denotes a phenyl radical;
$R^{2a}$ denotes methyl or one of the meanings of $R^{1a}$, including phenyl for all the meanings of $M^a$;
$R^{3a}$ denotes hydrogen or chlorine;
$X^a$ denotes fluorine, chlorine or bromine, but not fluorine when $M^a$ denotes zirconium or hafnium, and not chlorine when $M^a$ represents zirconium and $R^{1a}$ represents phenyl or when $M^a$ represents hafnium, $R^{1a}$ represents phenyl and $n^a$ represents the number 1, or if $M^a$ represents titanium and $R^{1a}$ represents p-fluoro-, p-chloro- or p-bromo-phenyl;
$m^a$ denotes the number 1 or 0 and
$n^a$ denotes the number 0, or, when $M^a$ denotes zirconium or hafnium, the number 1 or 0,
are new and are thus a further subject of the invention.

Compounds of formula $I^{a'}$ ($I^{a'}$)

wherein
$M^{a'}$ denotes zirconium or hafnium;
$R^{1a'}$ denotes phenyl;
$R^{2a'}$ denotes methyl;
$R^{3a'}$ denotes hydrogen or chlorine;
$X^{a'}$ denotes chlorine or bromine, but not chlorine when $M^{a'}$ represents zirconium or when $M^{a'}$ represents hafnium and $n^{a'}$ represents the number 1;
$m^{a'}$ denotes the number 1 or 0 and
$n^{a'}$ denotes the number 1 or 0;
are preferred.

Dichlorobis(benzoylacetonato)hafnium(IV), dibromobis(benzoylacetonato)zirconium(IV) and dibromobis(benzoylacetonato)hafnum(IV) are particularly preferred.

The invention also relates to a process for the preparation of the compounds of formulae $I^a$ and $I^{a'}$, wherein $R^{1a}$ and $R^{1a'}$, $R^{2a}$ and $R^{2a'}$, $R^{3a}$ and $R^{3a'}$, $X^a$ and $X^{a'}$, and $m^a$ and $m^{a'}$ and $n^a$ and $n^{a'}$ have the previously-mentioned meanings, which is characterized in that a metal tetrahalide $M^aX_4^a$ or $M^{a'}X_4^{a'}$ (wherein $M^a$ and $M^{a'}$ and $X^a$ and $X^{a'}$ have the previously-indicated meanings) is reacted with a diketone $R^{1a}(CH_2)_{(ma)}C(O)CHR^{3a}C(O)$ $R^{2a}$ or $R^{1a'}(CH_2)_{(ma')}C(O)CHR^{3a'}C(O)R^{2a'}$ (wherein $R^{1a}$ and $R^{1a'}$, $R^{2a}$ and $R^{2a'}$, $R^{3a}$ and $R^{3a'}$ and $m^a$ and $m^{a'}$ have the previously-mentioned meanings) in the absence of moisture in an inert solvent.

The medicaments according to the invention are primarily administered intravenously, but also intramuscularly, intraperitoneally, subcutaneously, rectally or perorally. External application is also possible. Administration by intravenous injection or intravenous infusion is preferred.

The medicaments are produced by processes which are known per se, the complex compound being employed as such or, if appropriate, in combination with suitable pharmaceutical excipients. When the new pharmaceutical formulations contain pharmaceutical excipients in addition to the active compound, the content of active compound in these mixtures is from 0.1 to 99.5, preferably from 0.5 to 95, percent by weight of the total mixture.

In accordance with the invention, the active compound is used in any suitable form, provided that the establishment and maintenance of sufficient blood and tissue levels of active compound are ensured. This is achieved, for example, by oral or parenteral administration in suitable doses. The pharmaceutical formulation of the active compound is expediently in the form of unit doses appropriate for the desired administration. A unit dose is, for example, a tablet, a dragee, a capsule, a suppository or a measured volume of a powder, of a granular material, of a solution, of an emulsion or of a suspension.

"Unit dose" for the purpose of the present invention means a physically-discrete unit which contains an individual amount of the active ingredient in combination with a pharmaceutical excipient, the content of active compound in the unit dose corresponding to a fraction or a multiple of a therapeutic individual dose. An individual dose preferably contains the amount of active compound which is given in one administration and usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain, e.g., from about 0.1 to 500 mg, advantageously from 10 to 200 mg and in particular from 50 to 150 mg, of active compound.

In general, it has proved advantageous in human medicine to administer the active compound or compounds, when these are given parenterally, in a daily dose of from about 0.1 to about 5, preferably from 0.5 to 3 mg/kg of body weight, if appropriate in the form of several, preferably 1 to 3, individual administrations, to achieve the desired results. An individual administration contains the active compound or compounds in amounts of from about 0.1 to about 5, preferably from 1 to 3, mg/kg of body weight. Similar dosages are used for oral treatment The pharmaceutical formulation is administered, for therapeutic purposes, systemically 1 to 4 times daily at fixed or varying points in time, for example after each meal and/or in the evening.

However, it may be necessary to deviate from the dosages mentioned, and in particular to do so in accordance with the nature, body weight and age of the patient to be treated, the nature and severity of the disease, the nature of the formulation and of the administration of the medicament, and the time or interval over which administration takes place. Thus, in some cases it may be sufficient to manage with less than the noted amount of active compound, while in other cases such amount of active compound must be exceeded. As is customary in internal tumor therapy, treatment with the medicaments according to the invention are optionally combined with administration of other cytostatic agents having different action spectra in order to reduce the risk of side effects. When appropriate, treatment is optionally carried out in accordance with the principle of cyclic cytostatic therapy. In this therapy, each treatment is followed by a recovery phase.

The optimum dosage and mode of administration of the active compounds required in each particular case is easily determind by any expert on the basis of his expert knowledge.

The pharmaceutical formulations as a rule consist of the complexes and non-toxic, pharmaceutically acceptable medicinal excipients, which are used as an admixture or diluent in solid, semi-solid or liquid form, or as a means of encasing, for example in the form of a capsule, a tablet coating, a sachet or some other container for the therapeutically-active ingredient. An excipient, for example, optionally serves as a promoter of the absorption of the medicament by the body, as a formulating auxiliary, as a sweetener, as a flavor correctant, as a colorant or as a preservative.

Examples of forms for oral administration are tablets, dragees, hard and soft capsules, for example made of gelatin, dispersible powders, granules, aqueous and oily suspensions, emulsions, solutions or syrups.

Tablets optionally contain inert diluents, for example calcium carbonate, calcium phosphate, sodium phosphate or lactose; granulating agents and dispersing agents, for example maize starch or alginates; binders, for example starch, gelatin or gum acacia; and lubricants, for example aluminum stearate or magnesium stearate, talc or silicone oil. The tablets are optionally provided with a coating, which can also be such that delayed dissolution and absorption of the medicament in the gastrointestinal tract and hence, for example, better tolerance, a protracted effect or a retarded effect is achieved. Gelatin capsules alternatively contain the medicament mixed with a solid diluent, for example calcium carbonate or kaolin, or an oily diluent, for example olive oil, groundnut oil or paraffin oil.

Aqueous suspensions contain, if desired, suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitan fatty acid esters, such as polyoxyethylene sorbitan monooleate, or lecithin; preservatives, for example methyl or propyl hydroxybenzoate; flavoring agents; and sweeteners, for example sucrose, lactose, sodium cyclamate, dextrose or invert sugar syrup.

Oily suspensions contain, for example, groundnut oil, olive oil, sesame oil, coconut oil or paraffin oil, and thickeners, such as beeswax, hard paraffin or cetyl alcohol; and furthermore sweeteners, flavoring agents and antioxidants.

Water-dispersible powders and granules contain the complexes mixed, e.g., with dispersing agents, wetting agents and suspending agents, for example those already mentioned, as well as with sweeteners, flavoring agents and colorants.

Emulsions contain, for example, olive oil, groundnut oil or paraffin oil, in addition to emulsifying agents, such as gum acacia, gum tragacanth, phosphatides, sorbitan monooleate or polyoxyethylene sorbitan monooleate, and sweeteners and flavoring agents.

For parenteral administration of the medicament, sterile injectable aqueous suspensions, isotonic salt solutions or other solutions which contain dispersing agents or wetting agents and/or pharmacologically-acceptable diluents, for example propylene glycol or butylene glycol, and/or solubilizing agents, for example Tweens, Cremophors or polyvinylpyrrolidone, are used.

It is particularly advantageous to mix solutions of the complexes in an anhydrous organic solvent with solutions of hydrophilic polymers, such as polyvinylpyrrolidones (PVP) or polyoxyethylene sorbitan fatty acid esters (Tween ®) and, after stripping off the solvent or solvents, to administer the remaining residues in the form of aqueous solutions. Suitable organic solvents are, for example, chloroformandmethylene chloride, which are rendered anhydrous in the customary manner before being used. It is. advantageous to use the hydrophilic polymers in a 5- to 50-fold, preferably 10- to 35-fold, excess by weight with respect to the complexes. The polymers are alternatively introduced as such into solutions of the complexes. The residue which remains after stripping off the solvent or solvents is expediently freed as far as possible from solvent residues under a high vacuum. Solid crystalline or vitreous residues, or liquid or tacky residues are obtained, depending on the nature and amount of the hydrophilic polymer used. The latter residues are generally convertible into solid, in most cases waxy, products by cooling. In the context of the present invention, these residues are called coprecipitates. The aqueous solutions are prepared by treating the coprecipitates with water. PVP-coprecipitates as a rule dissolve at room temperature. Coprecipitates with polyoxyethylene sorbitan fatty acid esters are advantageously dissolved by warming the coprecipitate and the water to 25° to 60° C., preferably to 30° to 40° C., before they are combined. The present invention furthermore preferably relates to coprecipitates obtained from the complexes of the previously-mentioned formula I, wherein M, $R^1$, $R^2$, $R^3$, X, m and n have the noted meanings, and hydrophilic polymers, processes for the preparation of these coprecipitates and aqueous solutions containing these coprecipitates.

The coprecipitates include pharmacologically-acceptable coprecipitate of a hydrophilic polymer and metal complex of formula (I) wherein:

M is tin, titanium, zirconium or hafnium;
$R^1$ is —H or one of the meanings of $R^4$;
$R^2$ is methyl or one of the meanings of $R^4$;
$R^3$ is —H or chloro;
$R^4$ is phenyl or substituted phenyl, any substituent of which is a member selected from the group consisting of fluoro, chloro, bromo, nitro, $C_{(1-4)}$-alkyl, $C_{(1-4)}$-alkoxy and trifluoromethyl;
X is —Cl or —Br when X is zirconium or hafnium and is —Cl, —Br or —F when X is tin or titanium;
m is zero or one when $R^1$ is one of the meanings of $R^4$ and is one when $R^1$ is —H; and
n is zero when M is tin or titanium and is zero or one when M is zirconium or hafnium.

The active compound can also be in a micro-encapsulated form, if appropriate together with one or more of the indicated excipients or additives.

The complexes are prepared by methods which are known per se, by reacting a metal tetrahalide with the corresponding diketone, with careful exclusion of moisture, in inert solvents, such as benzene, n-hexane, diethyl ether, methylene chloride or chloroform. [Zirconium and hafnium complexes: M. Cox, J. Lewis and R. S. Nyholm, *J. Chem. Soc.*, 1964, 6113; tin complexes: W. Dilthey, *J. Prakt. Chemie* [2], 111, 147 (1925); W. Dilthey, *Ber. Deutsch. Chem. Ges.*, 36, 923 (1903); G. T. Morgan and H. D. K. Drew, *J. Chem. Soc.*, 1924, 373; W. H. Nelson, *Inorgan. Chem.*, 6, 1509 (1967); and R. W. Jones, Jr. and R. C. Fay, *Inorgan. Chem.*, 12, 2599 (1973); titanium complexes: N. Serpone and R. C. Fay, *Inorgan. Chem.*, 6, 1835 (1967)].

The reaction is expediently carried out in a dry inert gas atmosphere, for example under nitrogen. Solid metal tetrahalides are initially introduced into the reaction vessel as a suspension in the same solvent in which the diketone is dissolved, and the diketone solution is added dropwise. In the reaction of liquid metal tetrahalides, such as titanium tetrachloride, the diketone is expediently initially introduced into the reaction vessel as a solution in an inert solvent and the metal tetrachloride is added dropwise. It has proved advantageous to add between the theoretically required amount and 20% excess, preferably approximately 10% excess, of the diketone. The reaction is carried out at room temperature, with cooling or with heating, for example under reflux, depending on how vigorous it is. In order to bring the reaction to completion, it may be necessary to heat the reaction mixture under reflux for one to three days. It has proved advantageous, by passing dry nitrogen through the reaction mixture, to drive out the hydrogen halide which forms during the reaction. When the reaction has ended, any unreacted solid residues of tetrahalide or any undissolved hydrolysis products are filtered off under an inert gas atmosphere, before the reaction solution is either concentrated or cooled in order to precipitate the product.

The 1,3-diketones are known, orthey are prepared by methods which are known per se. For example, they are obtained by estercondensation of the corresponding aryl methyl ketone with ethyl acetate or of the corresponding ethyl arylacetate with sodium amide as the condensing agent (J. T. Adams and C. R. Hauser, *J. Amer. Chem. Soc.*, 66, 1220 [1944]). The 1,3-diketones are alternatively obtained by adding the corresponding aryl methyl ketone, dissolved in ethyl acetate, to a suspension of sodium in benzene or toluene (D. W. Brown, S. F. Dyke, M. Sainsbury and G. Hardy, *J. Chem. Soc. (c)*, 1971, 3219). A further possibility consists in reacting aryl methyl ketones with acetic anhydride in the presence of boron trifluoride [H. G. Walker and C. R. Hauser, *J. Amer. Chem Soc.*, 68, 2742 (1946)]. 2-Chloro-1,3-diketones are prepared by chlorinating the corresponding 1,3-diketone with sulfuryl chloride in ether [Macbeth, *J. Chem. Soc.*, 123, I, 1129 (1923)]. 1-Benzyl-1,3-diketones are prepared by condensation of the corresponding ethyl phenylacetate with the corresponding methyl ketone in the presence of sodium amide (A. Becker, *Helv. Chim. Acta*, 149, 1114 (1949)].

PREPARATION EXAMPLES

1.*Dibromobis(benzoylacetonato(zircoinium(IV)*

24 g of benzoylacetone, dissolved in 100 ml of dry diethyl ether, are added dropwise to a suspension of 10 g of zirconium tetrabromide in 200 ml of dry diethyl ether under a dry stream of nitrogen, during which the reaction mixture boils under reflux.

The reaction mixture is heated under reflux for 24 hours. The precipitate which forms is washed twice with 100 ml of diethyl ether each time and dissolved in about 250 ml of chloroform. This solution is concentrated until it starts to become turbid. On cooling to room temperature, a colorless crystal sludge precipitates. After recrystallization of this sludge three times, 1 g (8.5% of theory) of the title compound of melting point 220°–221° C. (red melt) is obtained.

2. Bromotris(benzoylacetonato)zirconium(IV)

13 g of benzoylacetone, dissolved in 100 ml of dry benzene, are added dropwise to a suspension of 11 g of zirconium tetrabromide in 200 ml of dry benzene under a stream of nitrogen and while boiling under reflux. The reaction mixture is boiled under reflux until the evolution of hydrogen bromide has ended. Light brown crystals precipitate when the resulting red-brown solution is cooled.

These crystals are treated with diethyl ether under reflux until the ether is no longer yellowish-colored. After drying the crystals under an oilpump vacuum, 10 g (57% of theory) of the title compound of melting point 156° C. are obtained.

3. Dichlorobis(benzoylacetonato) hafnium(IV)

15.2 g of benzoylacetone, dissolved in 100 ml of dry diethyl ether, are added dropwise to a suspension of 5 g of hafnium tetrachloride in 200 ml of dry diethyl ether under a stream of nitrogen and while boiling under reflux. After the mixture has been boiled under reflux for 24 hours, the formed precipitate is filtered off, washed twice with 100 ml of diethyl ether each time and dissolved in about 300 ml of chloroform. After being concentrated until it starts to become turbid, the solution is filtered and the filtrate is left to stand at −5° C.. The colorless precipitate is recrystallized from chloroform 3 g (33.7% of theory) of melting point 231°–232° C. (red melt) are obtained.

4. Dibromobis(benzoylacetonato)hafnium(IV)

2 g of benzoylacetone, dissolved in 100 ml of dry diethyl ether, are added dropwise to a suspension of 2 g of hafnium tetrabromide in 100 ml of dry diethyl ether under a stream of nitrogen and while boiling under reflux. When the evolution of hydrogen bromide has ended, the pink-colored precipitate is filtered off and extracted five times with diethyl ether under reflux, in each case for three hours. 1 g (25% of theory) of the title compound is obtained.

5. Dibromobis(benzoylacetonato)titanium(IV)

7.0 g (0.019 mole) of titanium tetrabromide, dissolved in 40 ml of dry benzene, are added to 8.0 g (0.050 mole) of benzoylacetone, dissolved in 100 ml of dry benzene. The reaction mixture is heated under reflux for 30 minutes, during which a dry stream of nitrogen is passed through the solution. After about 40 ml of solvent have been distilled off, the brownish-red product is collected, recrystallized twice from a benzene/hexane mixture and dried in vacuo at 80° C. Melting point: 210°–222° C.

6. Difluorobis(benzoylacetonato)titanium(IV)

17.4 g (0.108 mole) of benzoylacetone, dissolved in 85 ml of methylene chloride, are slowly added to a suspension of 5.40 g (0.0436 mole) of titanium tetrafluoride in about 350 ml of methylene chloride. A slow stream of dry nitrogen is passed through the reaction mixture, while stirring, until the evolution of hydrogen fluoride has ended, which takes about 20 hours. The yellow-orange solution is filtered and the filtrate is then concentrated under reduced pressure to approximately half its volume. On cooling the concentrate, a yellow product crystallizes out and is filtered off and dried in vacuo (yield: 11.0 g, which corresponds to 62% of the theoretically calculated amount). Melting point: 196°–198.5° C.

7. Dichlorobis(benzoylacetonato)titanium(IV)

2 ml (0.018 mole) of freshly distilled titanium tetrachloride are added to a solution of 8 g (0.05 mole) of benzoylacetone in 60 ml of benzene (dried over sodium wire and by azeotropic distillation with ethanol), during which the reaction mixture heats up and dense fumes of hydrogen chloride escape. The reaction mixture slowly becomes deep red. When the reaction has subsided, the solution is boiled under reflux until all the hydrogen chloride gas has been removed (for about 2.5 hours. On cooling the mixture, orange-colored crystals precipitate. After the supernatant solution has been decanted off, the crystals are washed with benzene and dried at room temperature under reduced pressure. Yield: 11.68 g of yellow-orange crystals. Melting point: 209°–210° C. (decomposition). The product is identified by spectroscopy, for example by NMR.

The following table shows further preparation examples together with their analysis values and melting points:

| [R¹C(O)CR³C(O)R²]₂TiX₂ | | | | Analysis: calculated found | | | Melting point [°C.] |
|---|---|---|---|---|---|---|---|
| R¹ | R² | R³ | X | C | H | X | (decomposition) |
|  | CH₃ | H | F | 63.4<br>63.02 | 6.09<br>6.15 | 7.72<br>8.02 | 210–216 |
|  | CH₃ | H | Cl | 59.43<br>59.46 | 5.71<br>5.75 | 13.52<br>13.25 | 165–175 |

-continued

| [R¹C(O)CR³C(O)R²]₂TiX₂ | | | | Analysis: calculated found | | | Melting point [°C.] |
|---|---|---|---|---|---|---|---|
| R¹ | R² | R³ | X | C | H | X | (decomposition) |
| 3,4-(CH₃O)₂-C₆H₃- | CH₃ | H | F | 54.55 54.01 | 4.92 4.91 | 7.7 7.2 | 226–229 |
| 3,4-(CH₃O)₂-C₆H₃- | CH₃ | H | Cl | 51.35 51.8 | 4.64 4.75 | | 215–220 |
| 3,4-(CH₃O)₂-C₆H₃- | CH₃ | H | Br | 44.32 44.47 | 4.0 4.04 | | 200 |
| 4-O₂N-C₆H₄- | CH₃ | H | F | 48.19 47.6 | 3.21 3.37 | | 200–203 |
| 4-O₂N-C₆H₄- | CH₃ | H | Cl | 45.19 45.90 | 3.01 3.23 | | 190–202 |
| 3-O₂N-C₆H₄- | CH₃ | H | F | 48.19 48.67 | 3.21 3.41 | | 209–221 |
| 3-O₂N-C₆H₄- | CH₃ | H | Cl | 45.19 45.19 | 3.01 3.33 | | 212–217 |
| C₆H₅- | CH₃ | Cl | Cl | 47.06 47.45 | 3.14 3.33 | | 160–162 |
| 4-Br-C₆H₄- | CH₃ | H | F | 42.43 41.86 | 2.83 2.86 | | 189–193 |
| 4-Br-C₆H₄- | CH₃ | H | Cl | 40.01 40.25 | 2.82 2.7 | | 230–238 |
| 4-Cl-C₆H₄- | CH₃ | H | Cl | 47.1 47.38 | 3.1 3.31 | | 216–220 |

-continued

| $[R^1C(O)CR^3C(O)R^2]_2TiX_2$ | | | | Analysis: calculated found | | | Melting point [°C.] |
|---|---|---|---|---|---|---|---|
| $R^1$ | $R^2$ | $R^3$ | X | C | H | X | (decomposition) |
| F—⟨O⟩— | $CH_3$ | H | F | 54.05<br>53.47 | 3.6<br>3.81 | | 220–225 |
| F—⟨O⟩— | $CH_3$ | H | Cl | 50.31<br>50.45 | 3.35<br>3.63 | | 210–220 |
| $[NO_2\text{-}⟨O⟩\text{-}C(O)CHC(O)CH_3]_2 SnCl_2$ | | | | 39.92<br>39.42 | 2.66<br>2.67 | | >250 |

8. Coprecipitates of dichlorobis(benzoylacetonato)titanium(IV)

100 mg of dichlorobis(benzoylacetonato)titanium-(IV) are dissolved in about 10 ml of anhydrous methylene chloride. A solution of 1 g of PVP 30 BT (polyvinylpyrrolidone having an average molecular weight of 38000 to 40000 and a visoosity K value of 30) or 2 g of Tween ® 60 (sorbitan monostearate of polyoxyethylene) in about 30 ml of anhydrous methylene chloride is added to the clear solution. The resulting solution is stirred for some Alternatively, the complex is dissolved in correspondingly more solvent and the polymer (as such) is introduced into the resulting solution. The solvent is strained off on a rotary evaporator. Solvent residues are removed by application of a high vacuum.

With PVP 30 BT, a reddish-yellow crystalline mass which has a solubility in water of about 8 mg per ml is obtained.

With Tween ® 60, a red oily liquid is obtained which becomes a tacky mass on cooling. In order to prepare aqueous solutions, it is expedient to warm the coprecipitate and the water to 30° to 40° C. before combining them. Up to about 17 mg of coprecipitate dissolve in1 ml of water.

PHARMACOLOGY

A. Tumor Model

1. Sarcoma 180 tumor model

In each case about $10^6$ sarcoma 180 tumor cells in 0.2 ml of physiological saline solution are transferred intraperitoneally (I.P.) to female NMRI mice which are about 6 weeks old and weigh 18 to 20 g. The tumor is kept in passage in the same mouse strain. The tumor cells are removed from freshly killed animals immediately before transplantation. On inoculation, the animals are randomized. 6 mice are used per dosage. Cisplatin and cyclophosphamide are used as the control substances. The number of control groups (untreated animals) is chosen such that it corresponds to about the square root of the total number of groups. The substances are injected intraperitoneally, in each case 24 hours after the transplantation, as suspensions in customary solubilizing agents, such as Tween ® (polyoxyethylene derivatives of sorbitan esters).

2. L 1210 leukemia tumor model in NMRI mice

Female NMRI mice about 6 weeks old and weighing 18 to 20 g are inoculated intraperitoneally with, in each case, about $10^6$ freshly removed tumor cells in 0.2 ml of physiological saline solution. The tumor is kept in passage in the same mouse strain. The number of animals, the size of the control group and the administration of the substances are the same as those given for the sarcoma 180 tumor model described under point 1.

3. Walker 256 carcinosarcoma tumor model

Female SD rats weighing about 150 g are inoculated with, in each case, about $10^6$ tumor cells in 0.5 ml of physiological saline solution. The tumor is kept in passage in rats of the same strain. The number of animals and the administration of the substances are the same as those for the sarcoma 180 tumor model described under point 1. 6 animals are used per dosage.

B. Experimental Results

The results from the sarcoma 180 tumor model described under point A 1 are summarized in Table I which follows. The stated dose was administered once at the start of the experiment, as described. The factor T/C given in per cent denotes the percentage increase in median survival time of the treated animals compared with the median survival time of the untreated control animals. In some cases, the cure rate, that is to say the number of cured animals in relation to the number of treated animals, is given in the Table, in parentheses after the factor T/C.

The experiment is discontinued as soon as the median survival time T/C of the treated animals has reached 300% of the median survival time of the untreated animals. In calculating the median survival time, the animals still alive at the end of the experiment are taken as being dead at the end of the experiment. The comparison compound cisplatin has a therapeutic action in a dose range from about 8 to 10 mg/kg, and most of the animals are cured. At a dose of about 20 mg/kg, the median survival time of the animals treated with cisplatin is already shorter than that of the untreated control animals.

TABLE I

| $[R^1C(O)CR^3C(O)R^2]_k MX$ | | | | | | Dose [mg/kg] | T/C [%] |
|---|---|---|---|---|---|---|---|
| $R^1$ | $R^2$ | $R^3$ | k | M | X | | |
| 4-nitrophenyl ($O_2N{-}C_6H_4{-}$) | $CH_3$ | H | 2 | Ti | $Cl_2$ | 160<br>229 | 115<br>188 |
| 3,4-dimethoxyphenyl ($H_3CO$, $H_3CO{-}C_6H_3{-}$) | $CH_3$ | H | 2 | Ti | $Cl_2$ | 168<br>241 | 191<br>300 |
| 3,4-dimethoxyphenyl ($H_3CO$, $H_3CO{-}C_6H_3{-}$) | $CH_3$ | H | 2 | Ti | $Br_2$ | 280 | 209 |
| 4-chlorophenyl ($Cl{-}C_6H_4{-}$) | $CH_3$ | H | 2 | Ti | $Cl_2$ | 102 | 173 |
| 4-bromophenyl ($Br{-}C_6H_4{-}$) | $CH_3$ | H | 2 | Ti | $F_2$ | 244 | 300 |
| 4-bromophenyl ($Br{-}C_6H_4{-}$) | $CH_3$ | H | 2 | Ti | $Cl_2$ | 180<br>258 | 300<br>300 |
| 2,4,6-trimethylphenyl (mesityl) | $CH_3$ | H | 2 | Ti | $Cl_2$ | 158<br>226 | 300<br>300 |
| phenyl ($C_6H_5{-}$) | $CH_3$ | H | 2 | Ti | $F_2$ | 4<br>15<br>38<br>52<br>75<br>113<br>162<br>238 | 97 (0/6)<br>115 (0/6)<br>209 (1/6)<br>300 (4/6)<br>154 (0/6)<br>300 (3/6)<br>300 (4/6)<br>300 (2/6) |
| phenyl ($C_6H_5{-}$) | $CH_3$ | H | 2 | Ti | $Br_2$ | 5<br>20<br>50<br>70<br>100<br>150<br>215<br>315 | 103 (0/6)<br>115 (0/6)<br>288 (1/6)<br>300 (3/6)<br>300 (3/6)<br>300 (4/6)<br>273 (1/6)<br>300 (5/6) |
| phenyl ($C_6H_5{-}$) | $CH_3$ | H | 2 | Ti | $Cl_2$ | 4<br>16<br>41<br>57<br>82<br>123<br>177<br>259 | 118 (0/6)<br>115 (0/6)<br>291 (2/6)<br>179 (0/6)<br>300 (4/6)<br>212 (1/6)<br>251 (1/6)<br>300 (5/6) |

TABLE I-continued

| \[R¹C(O)CR³C(O)R²\]ₖMX | | | | | | Dose | |
|---|---|---|---|---|---|---|---|
| R¹ | R² | R³ | k | M | X | [mg/kg] | T/C [%] |
|  |  | H | 2 | Ti | Br₂ | 63<br>92<br>111 | 203<br>300<br>280 |
|  |  | H | 2 | Ti | Cl₂ | 37<br>54<br>79 | 293<br>273<br>266 |
| —CH₂— |  | H | 2 | Ti | Cl₂ | 60<br>119 | 178<br>300 |
|  | CH₃ | H | 2 | Zr | Cl₂ | 31<br>46<br>68<br>97<br>145<br>208 | 234<br>300<br>300<br>300<br>193<br>144 |
|  | CH₃ | H | 3 | Zr | Cl | 85<br>195<br>439 | 137<br>300<br>222 |
|  | CH₃ | H | 2 | Zr | Br₂ | 54<br>80<br>126<br>172<br>247 | 300<br>300<br>191<br>172<br>184 |
|  | CH₃ | H | 3 | Zr | Br | 92<br>209<br>471 | 300<br>297<br>187 |
|  | CH₃ | H | 2 | Hf | Cl₂ | 114<br>172<br>246 | 130<br>267<br>300 |
|  | CH₃ | H | 3 | Hf | Cl | 98<br>223<br>502 | 220<br>300<br>287 |
|  | CH₃ | H | 2 | Sn | Cl₂ | 52,6 | 230 |
|  | CH₃ | H | 2 | Sn | Br₂ | 84 | 141 |
| Cisplatin | | | | | | 1<br>2<br>3<br>5<br>8<br>13<br>22 | 112 (0/6)<br>133 (0/6)<br>300 (2/6)<br>300 (5/6)<br>300 (6/6)<br>300 (6/6)<br>42 (0/6) |

Figure 1:
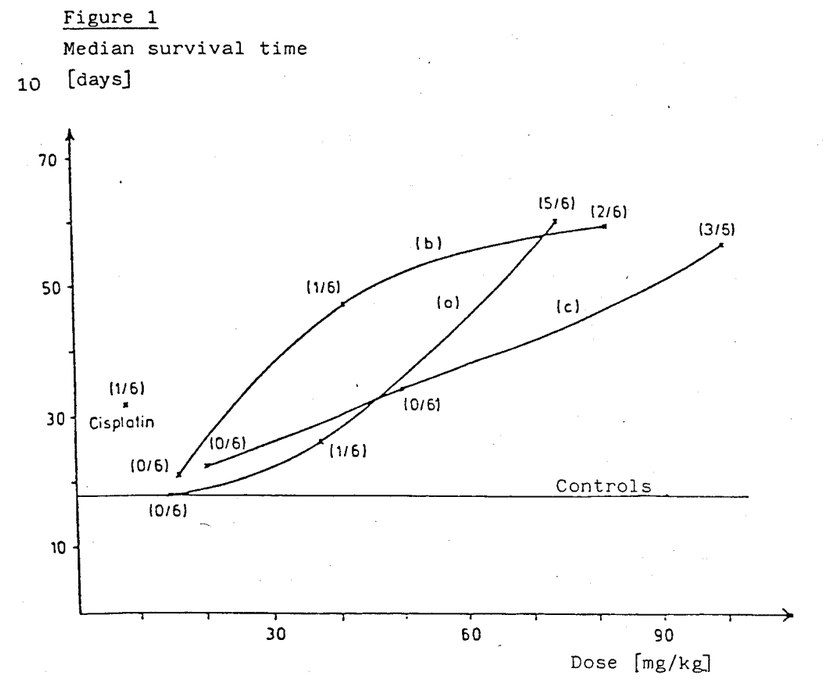
FIGS. 1 and 2 compare the invention to Cisplatin and controls with regard to median survival time in experiments on two cancer models.

FIG. 1 shows the results of comparison experiments with the L 1210 leukemia tumor model using the compounds difluorobis(benzoylacetonato)titanium(IV) [curve (a)], dichlorobis(benzoylacetonato)titanium(IV) [curve (b)], and dibromobis(benzoylacetonato)titanium(IV) [curve (c)]. the median survival time in days is plotted on the ordinate and the dose administered once at the start of the experiment is plotted on the abscissa. The median survival time of the untreated control animals (18 days) is shown as a horizontal line. In addition, the cure rates (number of cured animals per group of 6 animals) are given for the individual dosages, in parentheses. The experiments were discontinued after 60 days. Cisplatin was administered as the comparison substance in a dose of 8 mg/kg.

Figure 2:
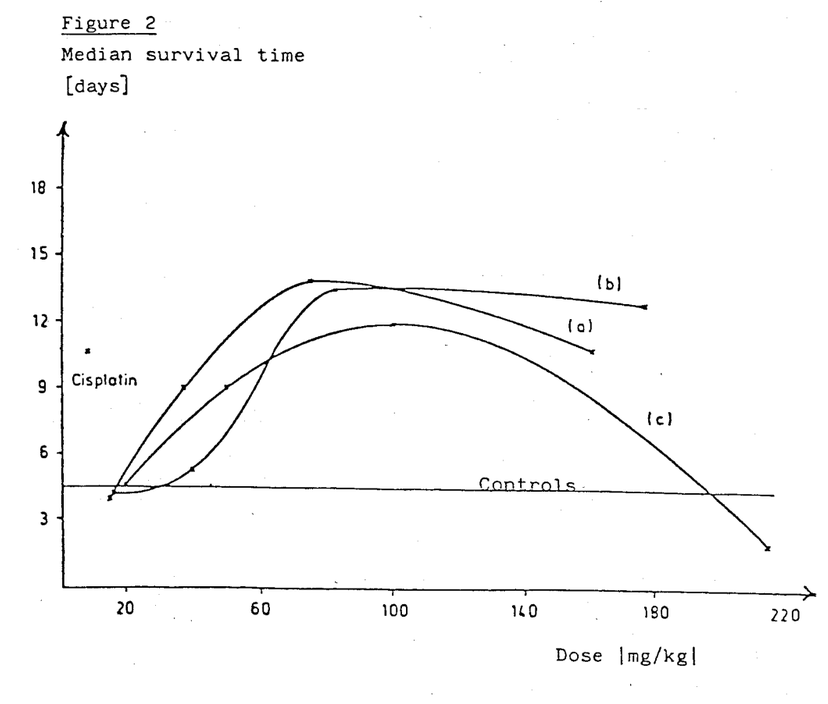

FIG. 2 shows the results of comparison experiments with the Walker 256 carcinosarcoma tumor model using the compounds difluorobis(benzoylacetonato)titanium-(IV) [curve (a)], dichlorobis(benzoylacetonato)titanium(IV) [curve (b)], and dibromobis(benzoylacetonato)titanium(IV) [curve (c)]. The median survival time in days is plotted on the ordinate and the dose administered once at the start of the experiment is plotted on the abscissa. The median survival time of the untreated control animals (4.5 days) is shown as a horizontal line.

These studies show that the complexes investigated are significantly more effective than cisplatin. At the same time, their toxicity is very much lower compared with that of cisplatin ($LD_{50}$ in mice and rats: 12 mg/kg). The nephrotoxicity known to exist in the case of cisplatin could not be observed with the complexes investigated.

In a further experiment, about $5 \times 10^6$ sarcoma 180 cells were subcutaneously transplanted into twelve female mice on day 0. From the 2nd week after the transplantation, six animals were given intravenous therapy with 4 mg/kg of dichlorobis(benzoylacetonato)titanium(IV) as a Tween ® 60 coprecipitate (1:20) in aqueous solution, twice weekly for 4 weeks. The treated animals were cured at the end of therapy, while the untreated control animals had approximately walnut-sized sarcomas, which in most cases were already centrally necrotized, and exulcerated at several points.

In a further experiment, about $5 \times 10^6$ Yoshida sarcoma cells were subcutaneously transplanted into female SD rats on day 0. In the second week, 4 mg/kg of dichlorobis(benzoylacetonato)titanium(IV) as a Tween ® 60 coprecipitate (1:20) in aqueous solution were administered intravenously twice. The tumor regressed. After a period of three weeks, plum-sized recidives had formed in two out of three animals. One animal was cured. The recidives were treated intravenously twice weekly with the original dose for four weeks. Both animals were cured. At this point in time, the control animals displayed extensive tumor growth and died a short time later.

The invention and its advantages are readily understood from the foregoing description. Various changes may be made in the complex compounds, in the co-precipitates, in the method of preparing the coprecipitates, in the compositions and in the methods of use without departing from the spirit and scope of the invention or sacrificing its material advantages. The products and methods described herein are merely illustrative of preferred embodiments of the invention.

What is claimed is:

1. A pharmaceutically-acceptable medicament composition comprising pharmaceutically-acceptable excipient and from 0.1 to 99.5 percent by weight of metal complex of the formula wherein M is tin, titanium, zirconium or hafnium;
$R^1$ is —H or one of the meanings of $R^4$;
$R^2$ is methyl or one of the meanings of $R^4$;
$R^3$ is —H or chloro;
$R^4$ is phenyl or substituted phenyl, any substituent of which is a member selected from the group consisting of fluoro, chloro, bromo, nitro, $C_{1-4}$-alkyl, $C_{(1-4)}$-alkoxy and trifluoromethyl;
X is —Cl or —Br when X is zirconium or hafnium and is —Cl, —Br or —F when X is tin or titanium;
m is zero or one when $R^1$ is one of the meanings of $R^4$ and is one when $R^1$ is —H; and
n is zero when M is tin or titanium and is zero or one when M is zirconium or hafnium;

the medicament composition being in the form of a tablet, dragee, capsule, suppository, powder, granular material, solution suitable for parenteral administration, emulsion, suspension or syrup.

2. A medicament composition according to claim 1 in unit dosage form and wherein
$R^1$ is one of the meanings of $R^4$;
$R^4$ is phenyl, 4-chlorophenyl, 4-bromophenyl, 3-nitrophenyl, 4-methoxyphenyl, 3,4-dimethoxyphenyl, 4-methylphenyl or 2,4,6-trimethylphenyl.

3. A medicament composition according to claim 1 wherein $R^1$ is phenyl and $R^2$ is methyl.

4. A medicament composition according to claim 2 in unit dosage form and comprising a member selected from the group consisting of dichlorobis(benzoylacetonato)titanium(IV), dichlorobis(benzoylacetonato)zirconium(IV) and dichlorobis(benzoylacetonato)hafnium(IV).

5. A composition of claim 1 wherein the metal complex is of the formula wherein

M is a member selected from the group consisting of tin, titanium, zirconium and hafnium;
$R^1$ is monosubstituted phenyl or polysubstituted phenyl when M is tin or titanium, and is phenyl, monosubstituted phenyl or polysubstituted phenyl when M is zirconium or hafnium; any substituent of monosubstituted or of polysubstituted phenyl being a member selected from the group consisting of fluoro, chloro, bromo, nitro, alkyl having from 1 to 4 carbon atoms, alkoxy having from 1 to 4 carbon atoms and trifluoromethyl;
$R^2$ is methyl, phenyl, monosubstituted phenyl or polysubstituted phenyl; any substituent of monosubstituted or of polysubstituted phenyl being among those enumerated in the definition of $R^1$;
$R^3$ is —H or chloro;
X is —F, —Cl or —Br when M is tin; is —F, —Cl or —Br when M is titanium and $R^1$ is other than p-fluorophenyl, p-chlorophenyl or p-bromophenyl; is —F or —Br when M is titanium and $R^1$ is p-fluorophenyl, p-chlorophenyl or p-bromophenyl; is —Cl or —Br when M is zirconium and $R^1$ is other than phenyl; is —Br when M is zirconium and $R^1$ is phenyl; is —Cl or —Br when M is hafnium and $R^1$ is other than phenyl and n is concurrently 1; and is —Br when M is hafnium, $R^1$ is phenyl and n is 1;
m is zero or one; and
n is zero when M is tin or titanium, and is zero or one when M is zirconium or hafnium.

6. A composition according to claim 5 wherein

M is zirconium or hafnium;
R¹ is phenyl;
R² is methyl;
R³ is —H or chloro;
X is —Cl or —Br;
m is zero or one; and
n is zero or one.

7. A composition according to claim 6 which is dichlorobis(benzoylacetonato)hafnium (IV).

8. A composition according to claim 6 which is dibromobis(benzoylacetonato)zirconium(IV).

9. A medicament composition according to claim 1 wherein the metal complex is dichlorobis(benzoylacetonato)titanium(IV).

10. A medicament composition of claim 1 wherein R¹ is a phenyl radical, which is optionally substituted by 4-chloro, 4-bromo, 3-nitro, 4-methoxy, 3,4-dimethoxy, 4-methyl or 2,4,6-trimethyl; R² is methyl or one of the meanings of R¹.

11. A pharmaceutically-acceptable medicament composition according to claim 1 and in unit dosage form, the composition comprising from 0.1 to 500 mg of metal complex per unit dose.

12. A pharmacologically-acceptable coprecipitate of a hydrophilic polymer and metal complex of the formula wherein
M is tin, titanium, zirconium, or hafnium;
R¹ is —H or one of the meanings of R⁴;
R² is methyl or one of the meanings of R⁴;
R³ is —H or chloro;
R⁴ is phenyl or substituted phenyl, any substituent of which is a member selected from the group consisting of fluoro, chloro, bromo, nitro, $C_{(1-4)}$-alkyl, $C_{(1-4)}$-alkoxy and trifluoromethyl;
X is —Cl or —Br when X is zirconium or hafnium and is —Cl, —Br or —F when X is tin or titanium;
m is zero or one when R¹ is one of the meanings of R⁴ and is one when R¹ is —H; and
n is zero when M is tin or titanium and is zero or one when M is zirconium or hafnium.

13. A coprecipitate according to claim 12 wherein the hydrophilic polymer is a polyvinylpyrrolidone.

14. A coprecipitate according to claim 12 wherein the hydrophilic polymer is a polyoxyethylene sorbitan fatty acid ester.

15. A coprecipitate according to claim 12 wherein the hydrophilic polymer is polyoxyethylene-20-sorbitan monostearate.

16. A coprecipitate according to claim 12 wherein the hydrophilic polymer is polyoxyethylene-20-sorbitan monooleate.

17. A coprecipitate according to claim 15 wherein the metal complex is dichlorobis(benzoylacetonato)titanium(IV).

18. A coprecipitate according to claim 16 wherein the metal complex is dichlorobis(benzoylacetonato)titanium(IV).

19. A coprecipitate according to claim 12 in which there is a 5 to 50-fold excess (by weight) of the hydrophilic polymer with respect to the metal complex.

20. A coprecipitate according to claim 19 wherein the hydrophilic polymer is a polyvinylpyrrolidone or a polyoxyethylene sorbitan fatty cid ester.

21. A sterile aqueous solution comprising a coprecipitate according to one of claims 12 to 18.

22. A medicament composition comprising pharmaceutically-acceptable excipient and 0.1 to 99.5% by weight of a coprecipitate according to claim 12.

23. A pharmaceutically-acceptable medicament composition according to claim 22 and in unit dosage form comprising from 0.1 to 500 mg of metal complex per unit dose.

* * * * *